United States Patent
McLoughlin

(10) Patent No.: US 8,192,463 B2
(45) Date of Patent: Jun. 5, 2012

(54) SURGICAL RETRACTOR AND RELATED METHODS

(76) Inventor: Joseph McLoughlin, Pompano Beach, FL (US)

( * ) Notice: Subject to any disclaimer, the term of this patent is extended or adjusted under 35 U.S.C. 154(b) by 904 days.

(21) Appl. No.: 12/110,398

(22) Filed: Apr. 28, 2008

(65) Prior Publication Data

US 2008/0294011 A1    Nov. 27, 2008

Related U.S. Application Data

(60) Provisional application No. 60/940,061, filed on May 24, 2007.

(51) Int. Cl.
*A61B 1/32* (2006.01)

(52) U.S. Cl. ........................................ 606/233
(58) Field of Classification Search ............... 600/233
See application file for complete search history.

(56) References Cited

U.S. PATENT DOCUMENTS

| | | | |
|---|---|---|---|
| 52,014 A | 1/1866 | Bartlett | |
| 55,511 A | 6/1866 | Leutz | |
| 151,228 A | 5/1874 | Knaffl | |
| 447,761 A | 3/1891 | Clough | |
| 497,064 A | 5/1893 | Meter | |
| 786,457 A | 4/1905 | McGinnis | |
| 1,400,616 A * | 12/1921 | McCrory et al. | 600/217 |
| 1,839,726 A | 1/1932 | Arnold | |
| 2,083,573 A | 6/1937 | Morgan | |
| 2,564,118 A | 8/1951 | Mahorner | |
| 2,586,488 A | 2/1952 | Smith | |
| 2,594,086 A | 4/1952 | Smith | |
| 3,038,468 A | 6/1962 | Raeuchle | |
| 3,394,700 A * | 7/1968 | Yamamoto | 600/234 |
| 3,749,088 A | 7/1973 | Kohlmann | |
| 3,893,454 A | 7/1975 | Hagelin | |
| 3,965,890 A | 6/1976 | Gauthier | |
| 3,998,217 A | 12/1976 | Trumbull et al. | |
| 4,130,113 A | 12/1978 | Graham | |
| 4,421,107 A | 12/1983 | Estes et al. | |
| 5,377,667 A | 1/1995 | Patton et al. | |
| 5,449,374 A | 9/1995 | Dunn et al. | |
| 5,505,690 A | 4/1996 | Patton et al. | |
| 5,512,037 A | 4/1996 | Russell et al. | |
| 5,554,101 A | 9/1996 | Matula et al. | |
| 5,588,951 A | 12/1996 | Zhu et al. | |
| 5,667,481 A | 9/1997 | Villalta et al. | |
| 5,688,223 A | 11/1997 | Rosendahl | |
| 5,716,326 A | 2/1998 | Dannan | |
| 5,868,668 A | 2/1999 | Weiss | |
| 5,885,219 A | 3/1999 | Nightengale | |

(Continued)

*Primary Examiner* — Thomas C. Barrett
*Assistant Examiner* — Sameh Boles
(74) *Attorney, Agent, or Firm* — Allen, Dyer, Doppelt, Milbrath & Gilchrist, P.A

(57) ABSTRACT

A surgical retractor includes a base defining an open area therein to correspond with a surgical incision in a body. The base has an inner wall facing the open area and an outer wall facing away from the open area. A plurality of channels extend through the base between the inner and outer walls, and at least one of the channels is at an angle offset from normal to the inner wall where the at least one channel intersects the inner wall. A respective retractor arm is carried within each of the channels for retracting the body to open the surgical incision. In a surgical method, such as a thyroidectomy, a base is positioned so that the open area corresponds with a surgical incision in a body. Respective retractor arms carried within each of the channels are moved to retract the body to open the surgical incision.

22 Claims, 6 Drawing Sheets

U.S. PATENT DOCUMENTS

| | | |
|---|---|---|
| 5,931,777 A | 8/1999 | Sava |
| 5,967,973 A | 10/1999 | Sherts et al. |
| 6,024,696 A | 2/2000 | Hoftman et al. |
| 6,213,940 B1 | 4/2001 | Sherts et al. ............ 600/231 |
| 6,346,078 B1 | 2/2002 | Ellman et al. ............ 600/235 |
| 6,354,995 B1 | 3/2002 | Hoftman et al. ............ 600/219 |
| 6,945,933 B2 | 9/2005 | Branch et al. ............ 600/210 |
| 2003/0176883 A1 | 9/2003 | Sauer et al. ............ 606/198 |
| 2005/0080320 A1 | 4/2005 | Lee et al. ............ 600/214 |
| 2005/0171405 A1 | 8/2005 | Rowland et al. ............ 600/233 |
| 2006/0074278 A1 | 4/2006 | Petit et al. ............ 600/224 |
| 2006/0142643 A1 | 6/2006 | Parker ............ 600/219 |
| 2006/0271096 A1 | 11/2006 | Hamada ............ 606/198 |
| 2007/0010716 A1 | 1/2007 | Malandain et al. ............ 600/224 |
| 2007/0038033 A1 | 2/2007 | Jones et al. ............ 600/219 |
| 2007/0043266 A1 | 2/2007 | Laucirica Gari ............ 600/228 |

* cited by examiner

SURGICAL RETRACTOR AND RELATED METHODS

CROSS-REFERENCE TO RELATED APPLICATION

This application claims the benefit of U.S. Provisional Application Ser. No. 60/940,061, filed on May 24, 2007, the contents of which are herein incorporated by reference in their entirety.

FIELD OF THE INVENTION

The present invention relates to surgical retractors and related methods.

BACKGROUND OF THE INVENTION

To properly perform invasive surgical procedures, it is often necessary to retract skin, muscle and other body tissue surrounding the surgical incision to allow the surgeon a clear view of the area to be operated on and room to use the required surgical tools.

Hand retractors are commonly employed for this purpose, typically handled by an assistant. An end of the hand retractor is inserted in the incision and moved to retract the desired tissue. However, hand retractors are often unwieldy, require frequent attention and tie up one or more hands of the assistant. Even if further assistants are available to the surgeon, the presence of too many personnel tends to crowd the surgical area.

Surgical retractors, usually including a basic frame with one or more retractors clamped thereto, are sometimes employed to alleviate the need for hand retractors and the corresponding dedicated personnel. However, such surgical retractors are often bulky, impeding access to the surgical incision, and frequently offer limited options concerning the manner in which retraction of the body around the incision is accomplished.

One example of an attempt to improve the utility of a surgical retractor can be seen in U.S. Pat. No. 1,400,616, in which an abdominal retractor has a frame contoured to fit a patient's body. A plurality of holes extend through the frame. Threaded stems with retraction fingers on an end thereof can be inserted through any of the holes. The holes are all oriented normal to the corresponding sections of the frame, resulting in limited options for the direction in which the body can be retracted around an incision. Additionally, the threaded stems require time-consuming screwing and unscrewing of a nut to secure the stems in a desired position.

Another example can be seen in U.S. Pat. No. 3,522,799, in which a surgical retractor has a plurality of support arms with retractor blades on ends thereof that can extend from respective portions of a frame at a variable angle. While the '799 patent offers increased options for body retraction around an incision, substantially increased bulk and complexity of equipment is required in exchange.

A further example can be seen in U.S. Patent Application Publication No. 2004/0242969 in which a surgical retractor has retractor blades that are adjustable using a ratchet and pawl system. While the ratchet and pawl system allows for quicker operation relative to the threaded stems of the '616 patent, the ratchet and pawl system also adds substantially to the overall bulk of the surgical retractor.

Additionally, while some surgical retractors offer basic contouring of the frame for areas such as the back or abdomen, surgical retractors shaped or contoured for more complex geometries are lacking.

SUMMARY OF THE INVENTION

In view of the foregoing background, it is therefore an object of the present invention to provide a surgical retractor and related methods that provide enhanced retraction features.

This and other objects, features, and advantages are provided by a surgical retractor including a base defining an open area therein to correspond with a surgical incision in a body, the base having an inner wall facing the open area and an outer wall facing away from the open area. A plurality of channels extend through the base between the inner and outer walls, and at least one of the channels is at an angle offset from normal to the inner wall where the at least one channel intersects the inner wall. A respective retractor arm is carried within each of the channels for retracting the body to open the surgical incision.

A method aspect may include positioning a base, such as the base briefly described above, so that the open area corresponds with a surgical incision in a body. Respective retractor arms carried within each of the channels are moved to retract the body to open the surgical incision.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
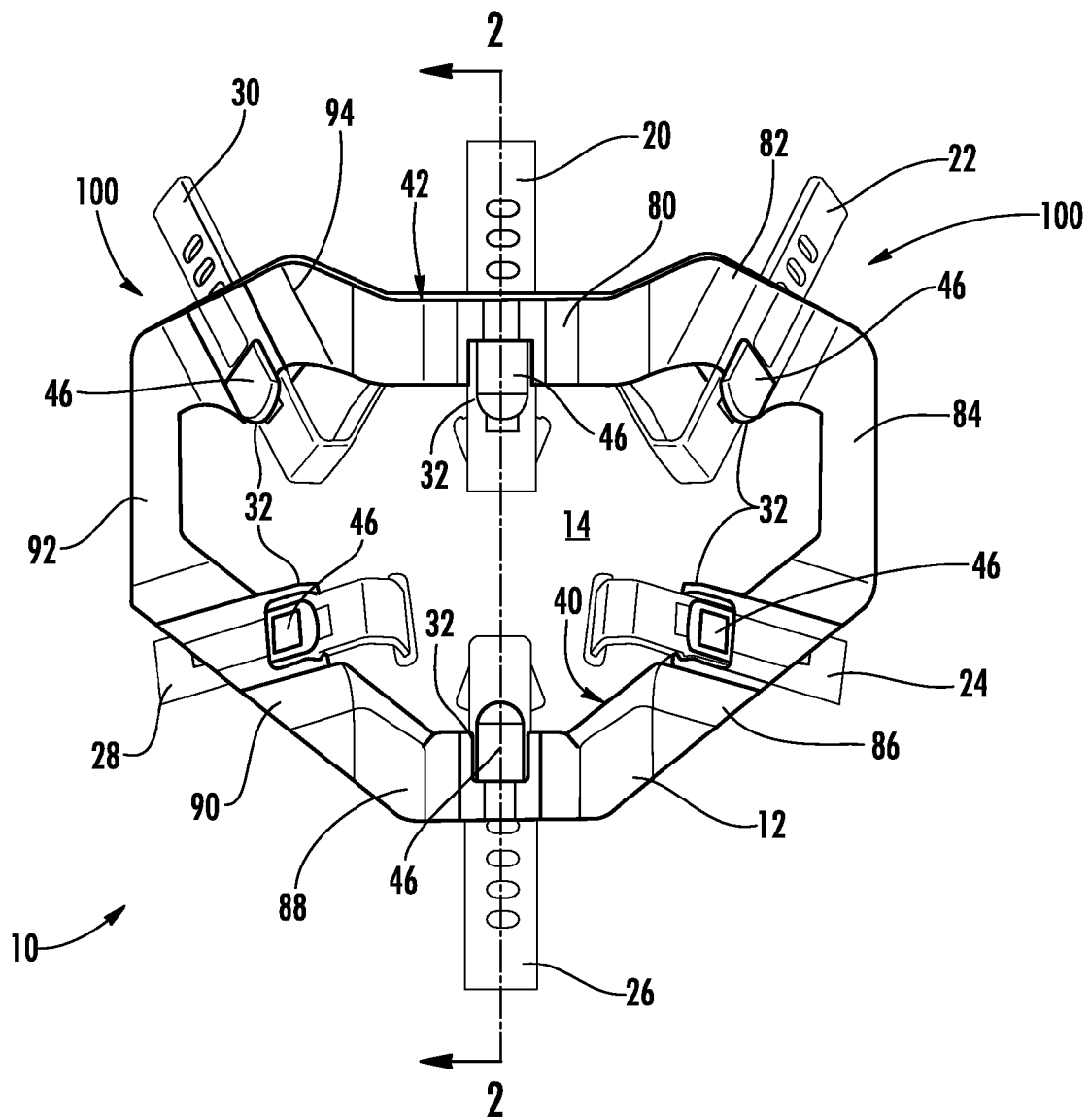
FIG. 1 is a front view of a surgical retractor including a base and a plurality of retractor arms, according to an embodiment of the present invention.

Referring initially to FIG. 1, a surgical retractor 10 illustratively includes a base 12 defining an open area 14 for disposing over a surgical incision in a body. In the embodiment shown, the base 12 completely surrounds the open area 14. However, other embodiments, in which the base 12 only partially surrounds the open area 14, are also possible. The retractor 10 further includes a plurality of retractor arms 20-30 slidably arranged in a plurality of channels 32 formed in the base 12.

Figure 2:
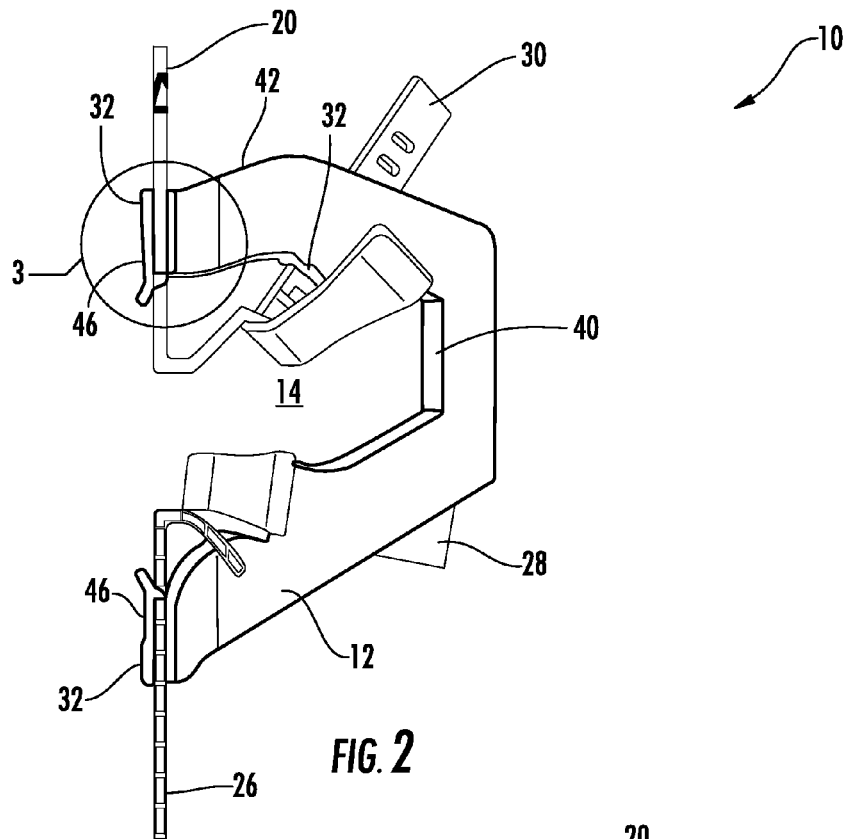
FIG. 2 is a cross-sectional view of the surgical retractor taken along line 2-2 of FIG. 1.

Referring to FIG. 2, the base 12 is formed with an inner wall 40 and an outer wall 42. The inner wall 40 substantially surrounds and faces the open area 14. The channels 32 extend through the base 12 between the inner wall 40 and the outer wall 42. Advantageously, the base 12 can be formed by plastic injection molding as a single piece, although other materials and forming techniques can also be employed. Moreover, the base 12 need not be a unitary piece in all embodiments.

Figure 3:
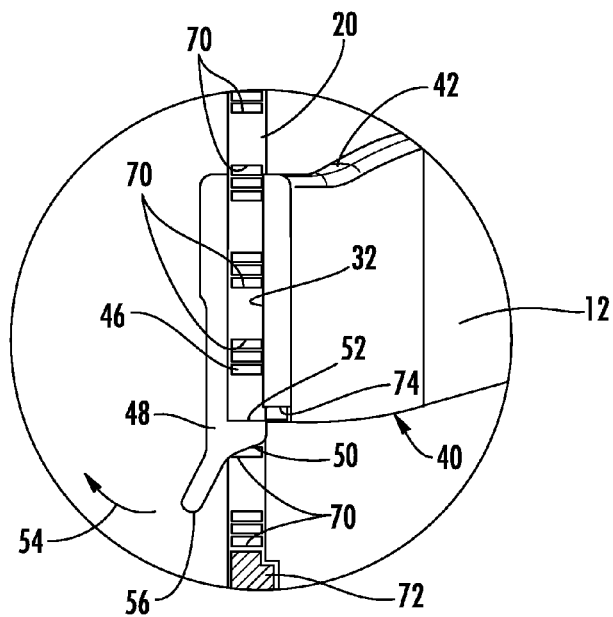
FIG. 3 is an enlarged view of area 3 of FIG. 2.
Figure 4:
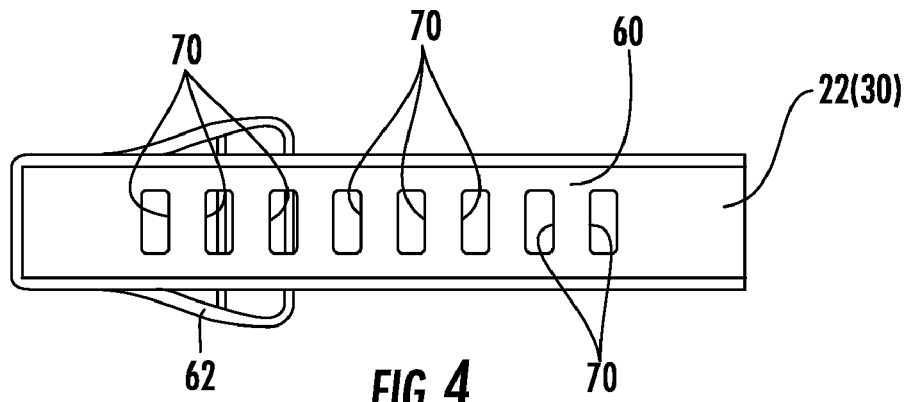
FIG. 4 is a top view of a retractor arm of FIG. 1.
Figure 5:
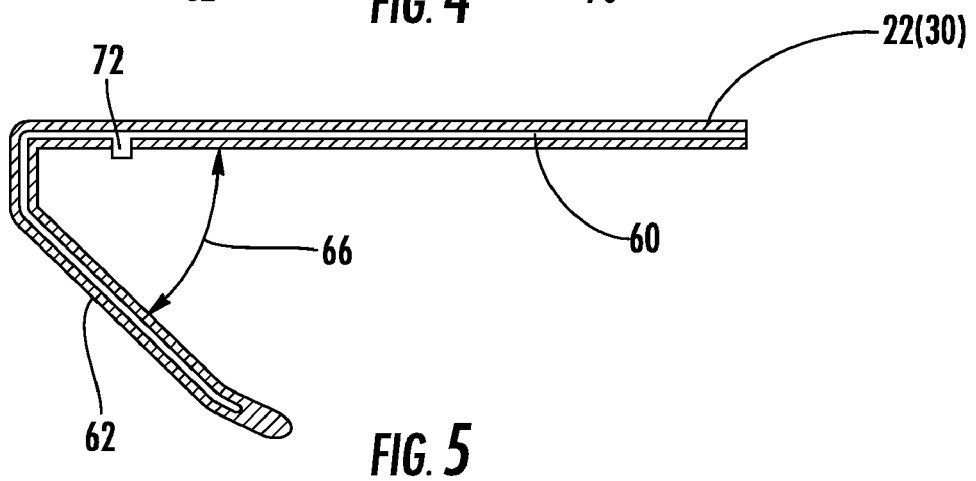
FIG. 5 is a side view of the retractor arm of FIG. 4.
Figure 6:
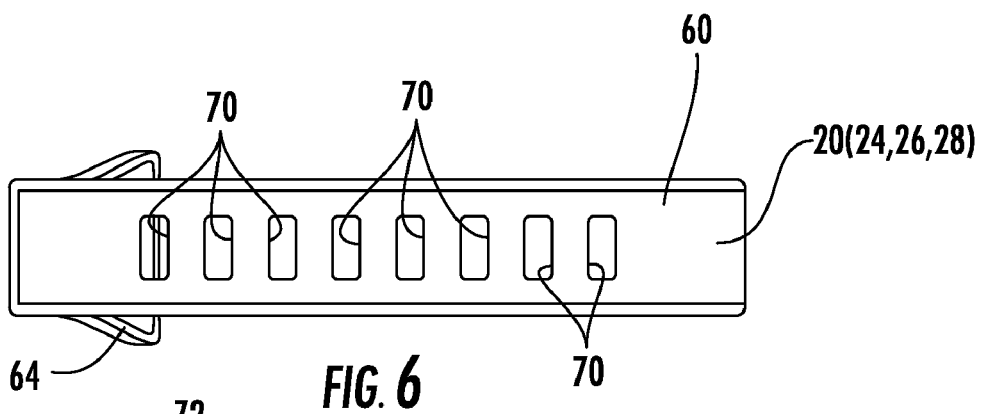
FIG. 6 is a top view of another retractor arm of FIG. 1.
Figure 7:
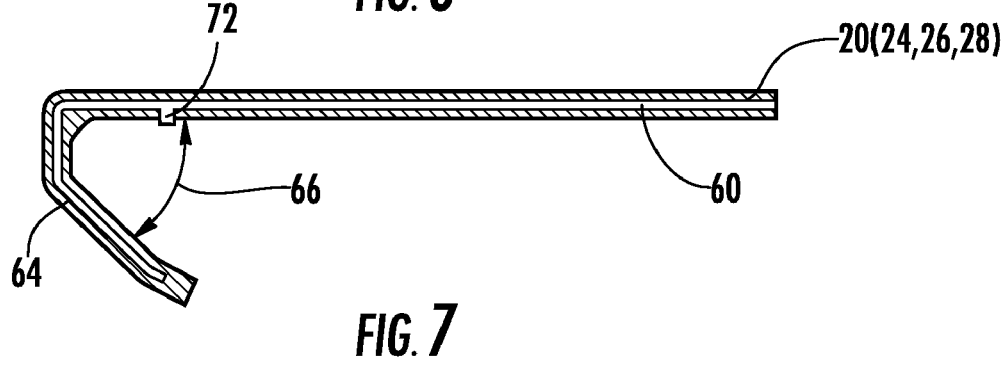
FIG. 7 is a side view of the retractor arm of FIG. 6.

Referring to FIG. 3, the base 12 includes a plurality of tabs 46 overlying the channels 32 (only one exemplary channel 32 and tab 46 are shown in FIG. 3 for clarity of illustration). The tabs 46 have posts 48 for engaging the retractor arms 20-30. The posts 48 include rounded surfaces 50 facing towards the open area 14 and flat surfaces 52 facing away from the open area 14.

The tabs 46 are flexible in the direction of arrow 54 to selectively disengage the posts 48 from the retractor arms 20-30. The resiliency of the tabs 46 is effective to bias the tabs 46 opposite the direction of arrow 54 when flexed. To facilitate manual flexion of the tabs 46, the tabs have distal ends 56 proximate to the posts 48, the distal ends 56 being angled away from the retractor arms 20-30. Other configurations and numbers of tabs and posts, as well as other locking mechanism designs, may also be used.

Referring to FIGS. 4-7, the retractor arms 20-30 include elongate sections 60 that are slidably disposed within respective channels 32. Body engagement extensions 62 depend from the elongate sections 60 of the retractor arms 22, 30, and body engagement extensions 64 depend from the elongate sections 60 of the retractor arms 20, 24-28. As will be appreciated from a comparison of FIGS. 4 and 5 with FIGS. 6 and 7, in the illustrated example the body engagement extensions 62 are longer than the body engagement extensions 64. However, the various body engagement sections may be the same length in some embodiments, or different sections may be different lengths or shapes. Body engagement extensions 62, 64 extend from the elongate sections 60 at an angle 66, for example an acute angle of forty-five degrees.

A plurality of holes 70 are defined within the elongate sections 60. The plurality of holes 70 are selectively engageable by the posts 48 of the tabs 46 (see FIG. 3), with engagement between the flat surfaces 52 and the holes 70 inhibiting further sliding of the retractor arms 20-30 into the open area 14 without flexion of the tabs 46 in the direction of arrow 54.

Safety stops 72 are also optionally formed on the elongate sections 60 of the retractor arms 20-30. The safety stops 72 extend outwardly from the elongate sections and engage recessed portions 74 of the inner wall 40 proximate to the channels 32 (see FIG. 3). The safety stops 72 inhibit the retractor arms 20-30 from being withdrawn to the point where the body engagement extensions 62, 64 engage the base 12. The safety stops 72 reduce the risk of pinching portions of the body in the area of the incision and the resultant physical trauma.

It will be appreciated that the surgical retractor 10 according the illustrated embodiment presents an extremely low profile (see also FIG. 8) having no bulky protrusions or added equipment to potentially restrict access to the surgical incision by a surgeon, although aspects of the present invention can be used in connection with surgical retractors having higher profiles and the like.

The combination of tabs 46 with posts 48 and holes 70 in the elongate sections are a particularly advantageous retractor arm locking mechanism in connection with a low profile surgical retractor, allowing a relatively high resistance to retractor arm disengagement when retracting the body for a relatively low overall height of the tabs 46 and posts 48. It will be understood that this locking mechanism can also be advantageously employed in connection with surgical retractors having higher profiles, and that other aspects of the present invention can be used in connection with surgical retractors having other locking mechanisms. Other suitable locking mechanisms may also be used.

The exemplary design of safety stops 72 illustrated herein is also advantageous in connection with low-profile surgical retractors, effectively operating to halt body retraction without substantially adding to the bulk or profile of the surgical retractor 10. Other safety stop 72 designs can also be employed in connection with the present invention, or safety stops 72 can be omitted if desired.

Surgical retractors including aspects and advantages of the present invention can be employed in connection with incisions on multiple sections of a human or animal body, and the present invention is not necessarily limited to any particular configuration or shape of the base or open area, or any particular configuration, shape or number of retractor arms.

However, the exemplary embodiment of a surgical retractor 10 shown and disclosed herein is particularly suitable for use in connection with a thyroidectomy and related procedures, in which the base 12 is positioned over a neck and clavicle section of the body.

Referring to FIG. 1, the base 12 is formed with a single line of symmetry (coincident with the sectional line 2-2). The base 12 has a plurality of segments 80-94, such that the inner wall 40 and outer wall 42 approximately define polygons. With reference to the orientation of FIG. 1, the segments 82, 94 are disposed above the segment 80, such that symmetrical lobes 100 are formed.

The segments 80, 82, 86-90, 94 have channels 32 extending therethrough for respective retractor arms 20-30. Segments 84, 92 do not have channels extending therethrough. The channels 32 extending through the segments 82, 86, 90, 94 are arranged at angles offset from normal relative to the segments 82, 86, 90, 94, and relative to where these channels 32 intersect the inner and outer walls 40, 42.

In the context of a thyroidectomy or related procedures, for segments 82, 94, an angle in an exemplary range of about ten to thirty degrees, and preferably about twenty degrees, from normal prevents interference between the retractor arms 22, 30 and the jaw. For segments 86, 90, an angle in an exemplary range of about twenty to forty degrees, and preferably about thirty degrees, from normal prevents interference between the retractor arms 24, 28 and the clavicles. Also, the lobes 100 allow segment 80 to be located below, relative to the orientation of FIG. 1, than segments 82 and 94. This exemplary arrangement maximizes the size of open area 14 while preventing interference between segment 80 and the underside of the chin, in a thyroidectomy or related procedure.

Figure 8:
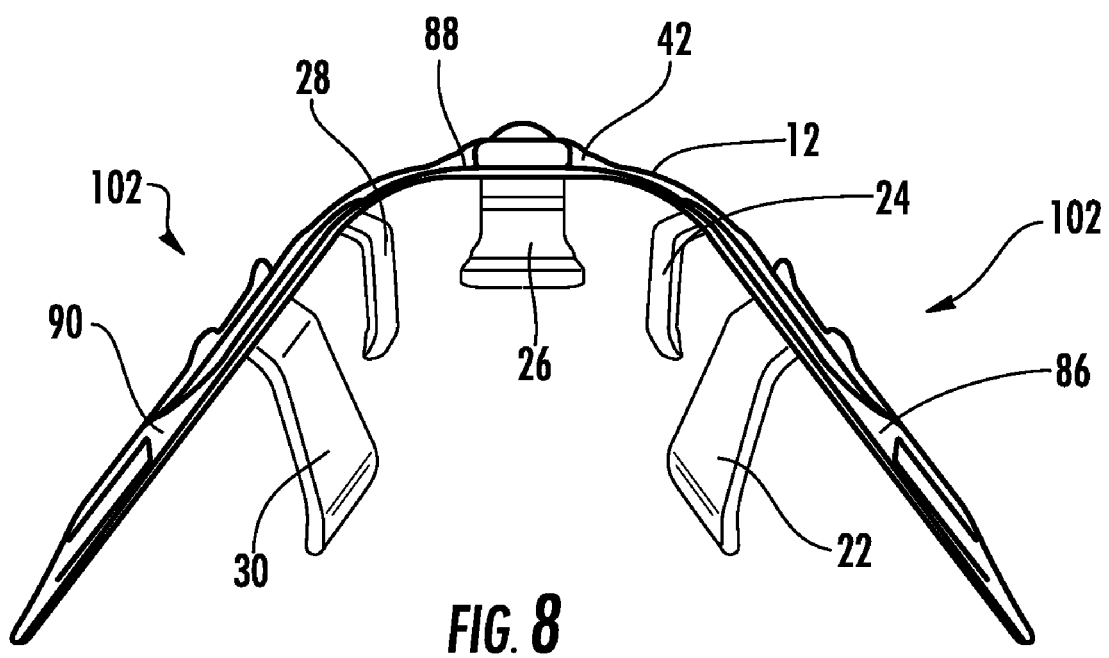
FIG. 8 is a bottom view of the surgical retractor of FIG. 1.

Referring additionally to FIGS. 1 and 8, the base 12 is contoured such that the segments 82-86 and segments 80-94 form respective wings 102 sloping away from segments 80 and 88. The base 12 between the wings 102 presents an approximately concave profile, facilitating placement of the surgical retractor 10 over corresponding convex section of the body, such as the neck and upper chest in the example of a thyroidectomy procedure.

Figure 9:
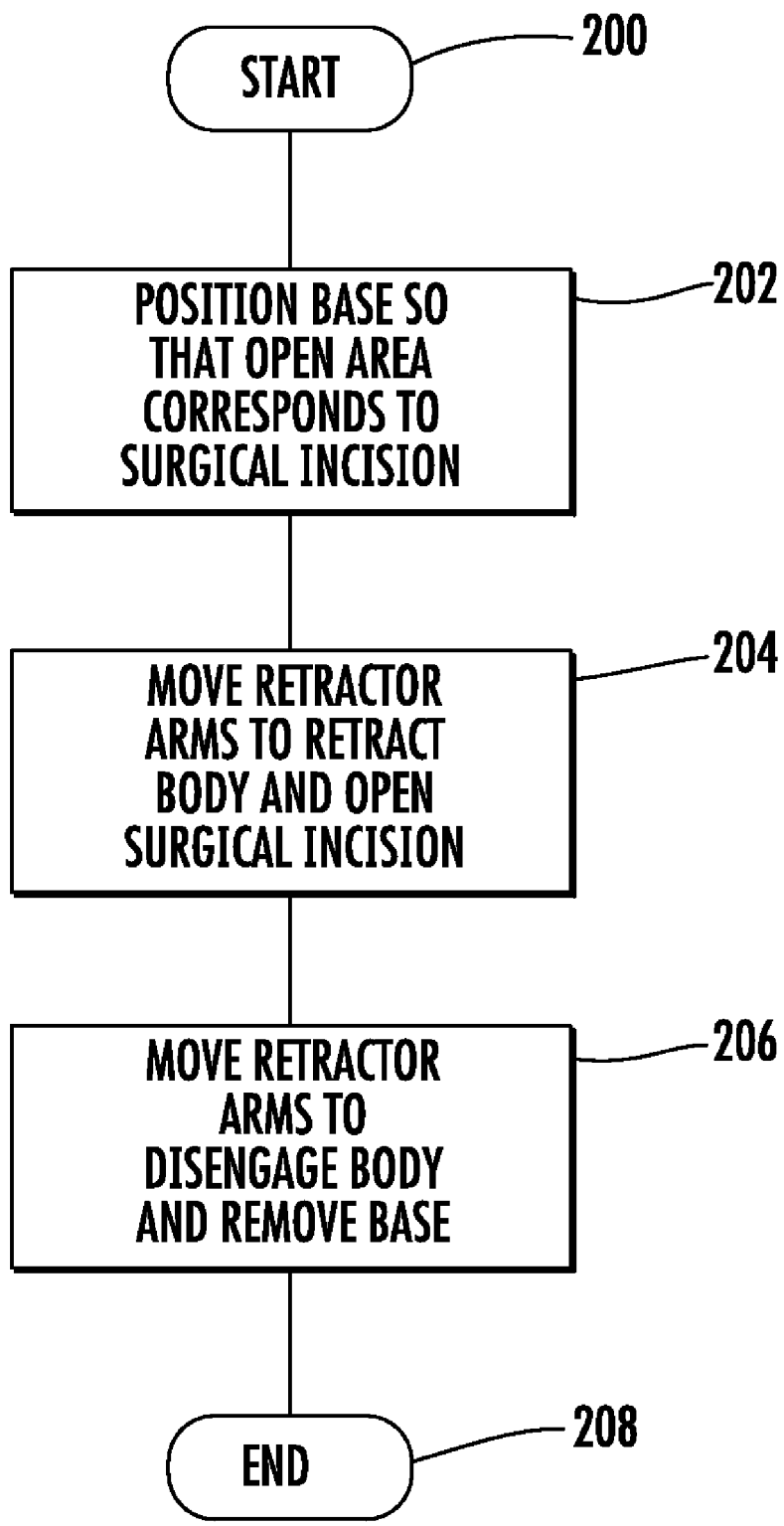
FIG. 9 is a flow diagram of a surgical procedure employing a surgical retractor according to an embodiment of the present invention.

Referring to FIG. 9, a surgical method, employing a surgical retractor according to an embodiment of the present invention, starts at block 200. For illustrative purposes, references will be made to the surgical retractor 10 described above. At block 202, the base 12 is positioned over the body so that the open area 14 corresponds to the surgical incision. Typically, the surgical incision is made before the base 12 is positioned over the body. However, the present invention is not necessarily limited to such a sequence and the base 12 can also be positioned over the body before the surgical incision is made. In such an instance, the open area 14 corresponds to the surgical incision in that the open area 14 corresponds to where the surgical incision will be made.

At block 204, the retractor arms 20-30 are moved to retract the body surrounding the surgical incision, opening the surgical incision. Moving the retractor arms 20-30 can be accomplished by manually gripping the elongate sections 60 to move the body engagement extensions 62, 64 toward the inner wall 40 of the base. As the retractor arms 20-30 are moved, rounded surfaces 50 of posts 48 engage edges of holes 70 resulting in flexion of tabs 46 in the direction of arrow 54. As a result, manual manipulation of tabs 46 is not normally employed when retracting the body. Over-retraction of the body by retractor arms 20-30 is prevented by the safety stops 72.

When retractor arms 20-30 are released, if posts 48 are in holes 70, engagement between flat surfaces 52 and edges of holes 70 will inhibit movement of body engagement extensions 62, 64 back into the open area 14, maintaining the body in the retracted position around the surgical incision. If posts 48 are not in holes 70 when retractor arms 20-30 are released and forces exerted by the retracted body act to move the body engagement extensions 62, 64 back into the open area 14, the resiliency of the tabs 46 will seat the posts 48 in adjacent holes 70. Uncontrolled release of retraction of the body is thereby limited to the distance between adjacent holes 70.

Once the surgical incision is opened, surgery is performed as necessary or desired. Once the surgery is complete or access through the open incision is no longer required, at block 206, the retractor arms 20-30 are moved to disengage the body and the base 12 is removed from the body. To move the retractor arms 20-30 to disengage the body, the distal ends 56 of the tabs 46 are manually engaged to flex the tabs 46 in the direction of arrow 54. Sufficient flexion of the tabs 46 disengages posts 48 from holes 70, allowing the body engagement extensions 62, 64 to be moved back in to the open area 14. At block 208, the method ends. Actions to close the incision and treat the body are performed as appropriate in coordination with the described procedure, as will be appreciated by those skilled in the art.

As described above, the exemplary embodiment of the surgical retractor described herein is particularly suitable for use in connection with thyroidectomy and related procedures. In connection with such procedures, the block 202 positioning of the base 12 includes positioning the base 12 over the neck and clavicle section of the body 12.

The open area 14 should surround the surgical incision in the neck, with the segment 88 resting near the junction of the clavicles. The concave contour between the wings 102 allows the base 12 to fit about the approximately convex profile of the neck. The positioning of segment 80 below lobes 100 allows additional clearance between the retractor arm 20 and the chin.

Figure 10:
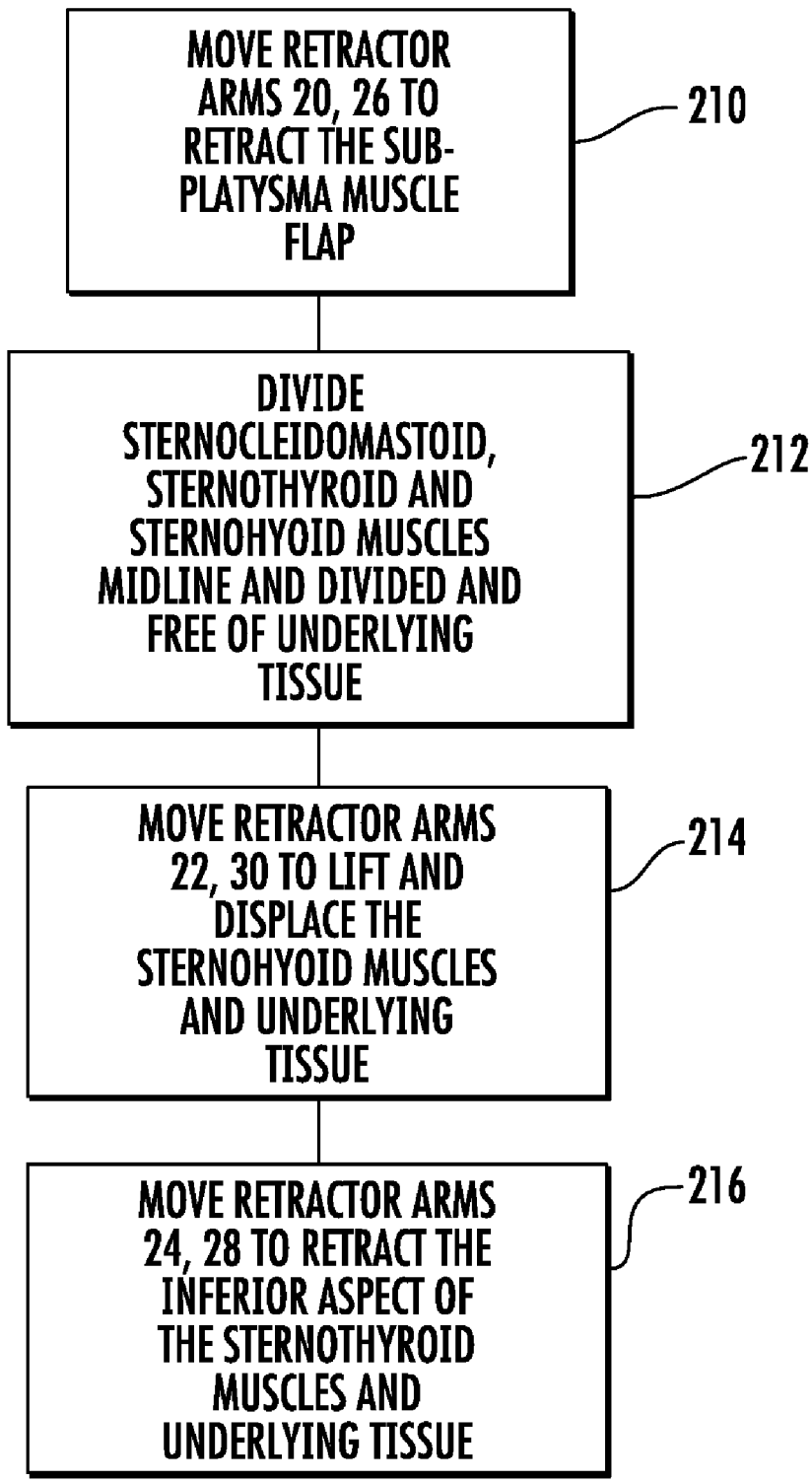
FIG. 10 is a flow diagram detailing a portion of the procedure of FIG. 9 in the context of a thyroidectomy or related procedure.

Referring to FIG. 10, an advantageous method of moving the retractor arms 20-30 to retract the body surrounding the surgical incision (as at block 204 of FIG. 9) in connection with a thyroidectomy or related procedure is described in greater detail. At block 210, the retractor arms 20, 26 are moved to retract the sub-platysma muscle flap created after the initial surgical incision is made.

At block 212, the Sternocleidomastoid, Sternothyroid and Sternohyoid muscles are divided midline and freed of underlying tissue. At block 214, the retractor arms 22, 30 are moved to lift and displace the Sternohyoid muscles and underlying tissue. As a result, a surgeon is provided with improved vision of the Superior Thyroid artery and Superior Thyroid vein for ligation, as well as the Superior Laryngeal nerve and Superior Parathyroid glands for preservation. Because of the angle at which the channels 32 route the retractor arms 22, 30 through the respective segments 82, 94, movement of the retractor arms 22, 30 does not interfere with the chin or jaw of the body.

At block 216, the retractor arms 24, 28 are moved to retract the inferior aspect of the Sternothyroid muscles and underlying tissue. As a result, ligation of the Inferior Thyroid artery and Inferior Thyroid vein, and preservation of the Recurrent Laryngeal nerve and Inferior Parathyroid glands, are facilitated. Because of the angle at which the channels 32 route the retractor arms 24, 28 through the respective segments 86, 90, movement of the retractor arms 24, 28 does not interfere with the clavicles of the body.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A surgical retractor comprising:
   a base having a polygonal shape and defining an open area therein to correspond with a surgical incision in a body, said base having an inner wall facing the open area and an outer wall facing away from the open area;
   said base having a plurality of channels therein extending between the inner and outer walls, and at least one of the channels being at an angle offset from normal to the inner wall where the at least one channel intersects the inner wall;
   a respective retractor arm carried within each of the channels for retracting the body to open the surgical incision.

2. The surgical retractor of claim 1 wherein the at least one channel comprises a plurality thereof.

3. The surgical retractor of claim 1 wherein at least one other of the plurality of channels is normal to the inner sidewall where the at least one other channel intersects the inner sidewall.

4. The surgical retractor of claim 1 wherein each of said retractor arms comprises:
   an elongate section slidably carried within a respective channel; and
   a body engagement extension carried by said elongate section within the open area for engaging the surgical incision.

5. The surgical retractor of claim 4 wherein each of said retractor arms further comprises a safety stop carried by said elongate section for engaging the inner wall of said base to prevent retraction of the incision beyond a safety limit.

6. The surgical retractor of claim 1 wherein the open area has a single axis of symmetry.

7. The surgical retractor of claim 1 wherein the open area has at least one lobe portion.

8. The surgical retractor of claim 1 wherein at least one of the inner walls and outer walls defines a polygon.

9. The surgical retractor of claim 1 wherein said base is contoured to fit over a section of the body.

10. The surgical retractor of claim 9 wherein the section of the body comprises and neck and clavicle section.

11. The surgical retractor of claim 1 wherein said base comprises an integral unit.

12. A surgical retractor comprising:
a base having a polygonal shape and defining an open area therein to be disposed over a surgical incision in a body, said base having an inner wall facing the open area and an outer wall facing away from the open area;
said base having a plurality of channels therein extending between the inner and outer sidewalls, at least one of the channels being at an angle offset from normal to the inner sidewall where the at least one channel intersects the inner sidewall, and at least one other of the plurality of channels being substantially normal to the inner sidewall where the at least one other channel intersects the inner sidewall;
a respective retractor arm carried within each of the channels for retracting the body to open the surgical incision, each retractor arm comprising:
an elongate section slidably carried within a respective channel; and
a body engagement extension carried by said elongate section within the open area for engaging the surgical incision.

13. The surgical retractor of claim 12 wherein the open area has a single axis of symmetry.

14. The surgical retractor of claim 12 wherein the open area has at least one lobe portion.

15. The surgical retractor of claim 12 wherein at least one of the inner walls and outer walls defines a polygon.

16. The surgical retractor of claim 12 wherein said base is contoured to fit over a neck and clavicle section of the body.

17. A surgical method comprising:
positioning a base having a polygonal shape and defining an open area therein so that the open area corresponds with a surgical incision in a body, the base having an inner wall facing the open area and an outer wall facing away from the open area;
the base also having a plurality of channels therein extending between the inner and outer sidewalls, and at least one of the channels being at an angle offset from normal to the inner sidewall where the at least one channel intersects the inner sidewall;
moving respective retractor arms carried within each of the channels to retract the body to open the surgical incision.

18. The method of claim 17 wherein the base is contoured; and wherein positioning the base comprises positioning the base over a neck and clavicle section of the body for performing a thyroidectomy.

19. The method of claim 17 wherein the at least one channel comprises a plurality thereof.

20. The method of claim 17 wherein at least one other of the plurality of channels is substantially normal to the inner sidewall where the at least one other channel intersects the inner sidewall.

21. The method of claim 17 wherein each of the retractor arms comprises:
an elongate section slidably carried within a respective channel; and
a body engagement extension carried by the elongate section within the open area for engaging the surgical incision.

22. The method of claim 21 wherein each of the retractor arms further comprises a safety stop carried by the elongate section for engaging the inner wall of the base to prevent retraction of the incision beyond a safety limit.

* * * * *